(12) United States Patent
Castle

(10) Patent No.: US 7,332,525 B2
(45) Date of Patent: Feb. 19, 2008

US007332525B2

(54) METHOD OF TREATMENT OF PROSTATE CANCER AND COMPOSITION FOR TREATMENT THEREOF

(76) Inventor: Erik P. Castle, 4111 N. Drinkwater Blvd., B 306, Scottsdale, AZ (US) 85251

(*) Notice: Subject to any disclaimer, the term of this patent is extended or adjusted under 35 U.S.C. 154(b) by 312 days.

(21) Appl. No.: 10/754,308

(22) Filed: Jan. 9, 2004

(65) Prior Publication Data

US 2004/0142973 A1 Jul. 22, 2004

Related U.S. Application Data

(60) Provisional application No. 60/440,937, filed on Jan. 17, 2003.

(51) Int. Cl.
*A61K 31/135* (2006.01)
*A61K 31/445* (2006.01)

(52) U.S. Cl. ........................... 514/649; 514/326

(58) Field of Classification Search ................. 514/649
See application file for complete search history.

(56) References Cited

U.S. PATENT DOCUMENTS

| | | | |
|---|---|---|---|
| 3,995,060 A | 11/1976 | Neri et al. | 424/324 |
| 4,133,814 A | 1/1979 | Jones et al. | 260/326.55 |
| 4,418,068 A | 11/1983 | Jones | 424/67 |
| 4,420,483 A | 12/1983 | Sunshine et al. | 424/253 |
| 4,474,813 A | 10/1984 | Neri et al. | 424/324 |
| 4,536,516 A | 8/1985 | Harper et al. | 514/514 |
| 4,636,505 A * | 1/1987 | Tucker | 514/256 |
| 4,895,715 A * | 1/1990 | Neri et al. | 514/171 |
| 5,023,088 A | 6/1991 | Wong et al. | 424/473 |
| 5,372,996 A | 12/1994 | Labrie | 514/15 |
| 5,593,987 A | 1/1997 | Cullinan et al. | 514/212 |
| 5,610,150 A * | 3/1997 | Labrie | 514/170 |
| 6,265,448 B1 | 7/2001 | Steiner et al. | 514/648 |
| 6,410,043 B1 | 6/2002 | Steiner et al. | 424/422 |
| 6,413,533 B1 | 7/2002 | Steiner et al. | 424/422 |
| 6,413,534 B1 | 7/2002 | Steiner et al. | 424/422 |
| 6,413,535 B1 | 7/2002 | Steiner et al. | 424/422 |
| 6,423,698 B1 | 7/2002 | Labrie | 514/169 |
| 6,468,981 B1 | 10/2002 | Petros et al. | 514/44 |
| 2001/0025051 A1 | 9/2001 | Cameron et al. | 514/422 |
| 2001/0036956 A1 | 11/2001 | Huebner et al. | 514/378 |
| 2002/0076695 A1 | 6/2002 | Ross | 435/6 |
| 2002/0103141 A1 | 8/2002 | McKearn et al. | 514/43 |
| 2002/0173445 A1 | 11/2002 | Salvati et al. | 514/1 |
| 2003/0114519 A1 | 6/2003 | Furr et al. | 514/522 |
| 2003/0134899 A1 | 7/2003 | Furr | 514/522 |

FOREIGN PATENT DOCUMENTS

| | | |
|---|---|---|
| EP | 0100172 | 2/1994 |
| WO | WO 93/10113 | 5/1993 |
| WO | WO 95/19770 | 7/1995 |
| WO | WO 01/89515 | 11/2001 |

OTHER PUBLICATIONS

Staiman, V.R. and Lowe, F.C. Tamoxifen for Flutamide/Finasteride-Induced Gynecomastia. Urology, 1997, 50: 929-933.*
Scher, H.I.; Liebertz, C.; Kelly, W.K.; Mazumdar, M.; Brett, C.; Schwartz, L.; Kolvenbag, G.; Shapiro, L.; Schwartz, M. Bicalutamide for advanced prostate cancer: the natural versus treated history of disease. J. Clin. Oncol. Aug. 1, 1997: 2928-2938.*
Steiner, M.S.; Raghow, S.; Neubauer, B.L. Selective Estrogen Receptor Modulators for the Chemoprevention of Prostate Cancer. Urology, 2001, 57 (Suppl 4A): 68-72.*
Hellerstedt et al., "The Current State of Hormonal Therapy for Prostate Cancer", *CA Cancer J. Clin.*, (vol. 52 No. 3, pp. 154-179 (May/Jun. 2002).
Bryant, "Selective Estrogen Receptor Modulators" *Review in Endocrine & Metabolic Disorders*, pp. 231-241 (2002).
Raghow et al., "Toremifene Provents Prostate Cancer in the Transgenic Adenocarcinoma of Mouse Prostate Model[1]", *Cancer Research* vol. 62 No. 5, pp. 1370-1376 (Mar. 2002).
Nanni et al., "Signaling through estrogen receptors modulates telomerase activity in human prostate cancer", *J. Clin. Invest.* vol. 110, No. 2, pp. 219-227 (Jul. 2002).
Kim et al., "Raloxifene, a Selective Estrogen Receptor Modulator, Induces Apoptosis in Androgen-responsive Human Prostate Cancer Cell Line LNCaP through an Androgen-independent Pathway", *Cancer Research*, vol. 62, No. 3, pp. 3649-3653 (Jul. 2002).
Kim et al., "Raloxifene, a Mixed Estrogen Agonist/Antagonist, Induces Apoptosis in Androgen-independent Human Prostate Cancer Cell Lines", *Cancer Research* vol. 62, pp. 5365-5369 (Sep. 2002).

(Continued)

*Primary Examiner*—Ardin H. Marschel
*Assistant Examiner*—James D. Anderson
(74) *Attorney, Agent, or Firm*—McCracken & Frank LLP

(57) ABSTRACT

A method and composition for the treatment of prostate cancer comprises an effective amount of a nonsteroidal antiandrogen and an effective amount of a selective estrogen receptor modulator. The composition has fewer side effects such as breast tenderness and gynecomastia and also is more effective as an adjuvant therapy to prevent the reoccurrence of prostate cancer.

9 Claims, No Drawings

OTHER PUBLICATIONS deLaunoit et al., "Characteristics of the Biphasic Action of Androgens and of the Potent Antiproliferative Effects of the New Pure Antiestrogen EM-139 on Cell Cycle Kinetic Parameters in LNCaP Human Prostatic Cancer Cells", *Cancer Research* vol. 51, pp. 5165-5170 (Oct. 1991).

Maucher et al., "Antiproliferative activity of casodex ICI (176.334) in hormone-dependent tumours", *J. Cancer Res. Clin. Oncol.*, vol. 119, pp. 669-674, (1993).

Pienta et al., "Inhibition of Prostate Cancer Growth by Vinblastine and Tamoxifen", *The Prostate*, vol. 26 pp. 270-274 (1995).

Viljoen et al. "Binding of Estradiol to Whole Prostatic DU-145 Cells in the Presence and Absence of Tamoxifen and Acetylsalicylic Acid", *The Prostate*, vol. 27, pp. 160-165 (1995).

Neubauer et al. "Raloxifene (LY156758) Produces Antimetastatic Responses and Extends Survival in the PAIII Rat Prostatic Adenocarcinoma Model", *The Prostate*, vol. 27 pp. 220-229 (1995).

Lucia et al., "Chemopreventive Activity of Tamoxifen, N-(4-Hydroxyphenyl)retinamide, and the Vitamin D Analogue Ro24-5531 for Androgen-promoted Carcinomas of the Rat Seminal Vesicle and Prostate", *Cancer Research*, vol. 55 pp. 5621-5627 (Dec. 1, 1995).

Urquhart, "Patient Compliance with Crucial Drug Regimens: Implications for Prostate Cancer", *Eur. Urol.* vol. 29, Supple. 2, pp. 124-131(1996).

Pienta et al., "A Phase II Evaluation of Oral Tamoxifen and Intermittent Intravenous Vinblastine in Hormone-Refractory Adenocarcinoma of the Prostate", *Am. Oncol. (CCT)*, vol. 19, No. 5, pp. 500-503 (1996).

Staiman et al., "Tamoxifen for Flutamide/Finasteride-Induced Gynecomastia", *Urology*, vol. 50, No. 6, pp. 929-933 (1997).

Rohlff et al., "Prostate Cancer Cell Growth Inhibition by Tamoxifen is Associated with Inhibition of Protein Kinase C and Induction of p21", pp. 51-59, *The Prostate*, vol. 37 (1998).

Serels et al., "Tamoxifen as Treatment for Gynecomastia and Mastodynia Resulting From Hormonal Deprivation" *J. Urology*, vol. 159, p. 1309 (Apr. 1998).

Braunstein, "Aromatase and gynecomastia", *Endocrine-Related Cancer*, vol. 6, pp. 315-324 (1999).

Richie, "Anti-Androgens and Other Hormonal Therapies for Prostate Cancer", *Urology* vol. 54, No. 6A, pp. 15-18 (Dec. 1999).

Bergan et al., "A Phase II Study of High-Dose Tamoxifen in Patients with Hormone-refractory Prostate Cancer[1]", *Clin. Cancer Res.* vol. 5, pp. 2366-2373 (Sep. 1999).

El Etreby et al., "Induction of Apoptosis by Mifepristone and Tamoxifen in Human LNCaP Prostate Cancer Cells in Culture", *The Prostate*, vol. 43, pp. 31-42 (2000).

Lau et al., "Expression of Estrogen Receptor (ER)-α and ER-β in Normal and Malignant Prostatis Epithelial Cells: Regulation by Methylation and Involvement in Growth Regulation[1]", *Cancer Research*, vol. 60, pp. 3175-3182 (Jun. 2000).

Taplin et al., "The Endocrinology of Prostate Cancer" pp. 3467-3477, *The Journal of Clinical Endocrinology & Metabolism*, vol. 86, No. 8, pp. 3467-3477 (Aug. 2001).

Lin et al., "A Pilot Study of AFL-T (Doxorubicin, 5-Fluorouracil, Leucovorin, and Tamoxifen) Combination Chemotherapy for Hormone Refractory Prostate Cancer", *Anticancer Research*, vol. 21 (2B) pp. 1385-1390 (2001).

Steiner et al., "Selective Estrogen Receptor Modulators for the Chemoprevention of Prostate Cancer", *Urology*, vol. 57, Suppl. 4A, pp. 68-72, (Apr. 2001).

Stein et al., "Phase II Trial of Toremifene in Androgen-Independent Prostate Cancer", pp. 283-285, *Am. Oncol. (CCT)*, vol. 24, No. 3 (2001).

Web page dated Nov. 5, 2002: http://www.phoenix5.org/Basics/reatsides/gyneLtrsBraunstein.html, Letters in the NEJM: Gynecomastia (5 pages).

Web page accessed Dec. 18, 2002 from: http://www.ncbi.nlm.nih.gov identifying an abstract of the article: Trump et al. "Androgen Antagonists: Potential Role in Prostate Cancer Prevention", *Urology*, vol. 57 (4 Suppl 1) (2001). (2 pages).

Web page accessed Dec. 19, 2002 from: http://www.ncbi.nlm.nih.gov identifying an abstract of the article: Kolar et al. "The Effects of Natural Ligands of Hormone Receptors and Their Antagonists on Telomerase Activity in the Androgen Sensitive Prostatic Cancer Cell Line LNCaP", *Biochem. Pharmacol.* vol. 63(6) (Mar. 2002). (2 pages).

Web page accessed Nov. 5, 2002 from: http://www.ncbi.nlm.nih.gov identifying an abstract of the article: Parker et al. "Treatment of Gynecomastia with Tamoxifen: A Double-blind Crossover Study", *Metabolism*, vol. 35(8) (Aug. 1996).

Int'l Search Report and Written Opinion dated Sep. 13, 2004, Appl. No. PCT/US2004/00668.

\* cited by examiner

METHOD OF TREATMENT OF PROSTATE CANCER AND COMPOSITION FOR TREATMENT THEREOF

CROSS-REFERENCE TO RELATED APPLICATIONS

This application claims priority under 35 U.S.C. § 119(e) to U.S. Provisional Appl. Serial No. 60/440,937, filed Jan. 17, 2003, the disclosure of which is incorporated in its entirety.

TECHNICAL FIELD

This invention relates to a method for the treatment of prostate cancer and a composition for the treatment of prostate cancer. This invention also relates to a method of treating prostate cancer that minimizes some of the undesirable side effects of the treatments.

BACKGROUND OF THE INVENTION

Prostate cancer is one of the most common forms of cancer for males in the developed world. In spite of the significant occurrence of this condition, the treatments of those males who have prostate cancer are less than optimal. Current efforts are on early detection and treatment. While this seems to have the greatest effect on survival by males, the primary treatments after early detection and diagnosis typically are surgery, brachytherapy, or external beam radiation. If the carcinoma has not metastasized, generally no adjuvant treatment after the primary treatment is indicated and the patient is monitored for reoccurrence of the cancer. However, if the carcinoma has metastasized, the current treatment after the primary treatment is androgen ablation. The present treatments for metastasized prostate cancer may fail over time as many patients ultimately develop hormone refractory prostate carcinoma that is resistant to the effects of androgen ablation.

Typical androgen ablation therapies include surgical or chemical castration or the administration of a combination of an LHRH agonist and a nonsteroidal antiandrogen drug, such as flutamide, bicalutamide, and nilutamide. The combination therapy is necessary because there still is some level of testosterone in the blood stream after treatment with castration or with the LHRH agonists. This residual level of testosterone is thought to come from secondary sources in the body, such as the adrenal gland. The nonsteroidal antiandrogen drugs block the binding of testosterone and its metabolite dihydrotestosterone to the androgen receptor in the cancer cells and thereby inhibit cell proliferation.

The drugs used in the treatment of prostate cancer also have differing but significant side effects for the majority of males, including impotence, hot flashes, gynecomastia, breast tenderness, liver toxicity, osteoporosis, depression, heart disease, gastro-intestinal disorders, and loss of cognitive function. The primary side effects for the nonsteroidal antiandrogen drugs include gynecomastia, breast tenderness, and gastro-intestinal disorders. These side effects are often so significant that many patients stop treatment with these drugs with the increased risk of progression of the cancer. See European Urology 1996 :29 (suppl 2): 124-131. At present, the gynecomastia and breast tenderness are treated either after the fact, sometimes by surgery to remove tissue, or the patient is treated with radiation prior to beginning the drug therapy. U.S. Pat. No. 4,895,715 discloses a method of treating gynecomastia in patients being treated with an antiandrogen for androgen dependent conditions such as benign prostatic hypertrophy by administering the antiandrogen in association with an antiestrogen compound, such as tamoxifen.

There has also been a proposal to treat prostate cancer with an adjuvant monotherapy involving only the nonsteroidal antiandrogen drugs, typically at a relatively high dose, after the primary treatment. This trial has been inconclusive as to the effectiveness of the nonsteroidal antiandrogen drugs to slow the reoccurrence of prostate cancer. However, there have been studies that show that bicalutamide seems to have a role in cancer cell death.

It has also been known that prostate cancer cells have estrogen receptors. For this reason, Bergan, et al (Clinical Cancer Research, Volume 5, pages 2366-2373, September 1999) proposed the treatment of prostate cancer with high doses of tamoxifen, a selective estrogen receptor modulator (SERM). This study showed that high doses of tamoxifen alone have some effect on the prostate cancer cells for patients that have metastasized prostate cancer and also have hormone refractory prostate cancer.

Other SERM's, such as raloxifene and toremifene, also have been shown to have some effect on the progression of metastasized prostate cancer. In a manner similar to the tamoxifen study reference above, these SERM's have some effect on metastasized prostate cancer. Also, there have been studies that seem to show that SERM's have a role in prostate cancer cell death.

While there have been studies with low doses of nonsteroidal antiandrogen drugs and there is one current study with a high dose of nonsteroidal antiandrogen drugs, at the present time, for patients without metastasized prostate cancer, there is no adjuvant treatment as a follow on treatment after the primary treatment. One reason for this is the side effects as described above of the drugs used for treatment of prostate cancer and the concern that these drugs have minimal inhibitory effect on the progression of prostate cancer compared to the efficacy of the LHRH analogs.

SUMMARY OF THE INVENTION

One aspect of the present invention is a pharmaceutical composition adapted to treat prostate cancer in a patient in need of such treatment comprising in a unit dosage form a therapeutically effective amount of a non-steroidal antiandrogen and a therapeutically effective amount of a selective estrogen receptor modulator to potentiate the non-steroidal antiandrogen.

A yet further aspect of the method of the present invention for treating prostate cancer in a patient in need of such treatment comprises the steps of administering a combination of a therapeutically effective amount of the non-steroidal antiandrogen and a non-steroidal antiandrogen potentiating adjuvant therefore, the adjuvant consisting essentially of a non-steroidal antiandrogen potentiating amount of a selective estrogen receptor modulator.

DETAILED DESCRIPTION OF THE PRESENT INVENTION

The present invention provides a safe and effective method of providing adjuvant therapy to patients suffering from early and later stages of prostate cancer. While in the past, adjuvant therapy was made available only to those patients with advanced stages of prostate cancer as indicated by the metastasized nature of the cancer, the present invention now finds that a combination therapy of two classes of drugs that have been used to treat prostate and other cancers can provide greater suppression of the prostate cancer and a more efficacious early treatments for all forms of prostate cancer. More particularly, the present invention finds that a combination of a nonsteroidal antiandrogen and a selective estrogen receptor modulator compound produce a better result that either drug taken separately.

As noted above, the particular nonsteroidal antiandrogens that are useful in the present invention include bicalutamide, flutamide, and nilutamide, and mixtures thereof.

Bicalutamide is the generic name for propanamide, N-[14-cyano-3-(trifluoromethyl)phenyl]-3-[(4-fluorophenyl)sulfonyl]-2-hydroxy-2-methyl-(+−), sold under the trade name Casodex. The preparation of bicalutamide is disclosed in U.S. Pat. No. 4,636,505, the disclosure of which is incorporated by reference herein. Bicalutamide is known for use in treatment of prostate cancer.

Flutamide is the generic name for 2-methyl-N-[4-nitro-3-(trifluoromethyl)phenyl] propanamide, sold under the trade name Eulexin. The preparation of flutamide is disclosed in U.S. Pat. Nos. 3,995,060, and 4,474,813, the disclosure of which are incorporated by reference herein. Flutamide is known for use in treatment of prostate cancer.

Nilutamide is the generic name for 5,5-dimethyl 3-[4-nitro 3-(trifluoromethyl)phenyl] 2,4-imidazolidinedione, sold under the trade name Nilandron. The preparation of nilutamide is disclosed in U.S. Pat. No. 5,023,088, the entire disclosure of which is incorporated by reference herein. Nalutamide is known for use in the treatment of prostate cancer.

Of these compounds, bicalutamide is most preferred, as it seems to offer the best efficacy to toxicity profile of the three compounds. The typical dosage for bicalutamide is between about 50 to 150 mg/day for a typical patient.

It is well known that treatment with nonsteroidal antiandrogens will lead to a significant incidence of breast tenderness, gynecomastia or both of these conditions. These side effects are well known and have been widely reported. In the past, recognized treatments for these side effects include pretreatment radiation to minimize the occurrence of the side effects or surgical treatment to remove tissue after the side effects have manifested themselves.

Suitable selective estrogen receptor modulators useful in the present invention include tamoxifen, raloxifene, and toremifene, and mixtures thereof.

Tamoxifen is generally available as tamoxifen citrate. Tamoxifen Citrate is the trans-isomer of a triphenylethylene derivative. The chemical name is (Z)2-[4-(1,2-diphenyl-1-butenyl) phenoxy]-N, N-dimethylethanamine 2-hydroxy-1,2,3-propanetricarboxylate (1:1). The compound is used in the treatment and prevention of breast cancer, and is believed to exert its anti-tumor effect through action as an anti-estrogen at estrogen receptor binding sites in breast tissue. The compound and its preparation are described in U.S. Pat. No. 4,536,516, the disclosure of which is incorporated by reference. Existing commercial formulations of tamoxifen citrate, such as NOLVADEX.RTM. (Zeneca Pharmaceuticals, Wilmington Del., USA), contain 10 mg or 20 mg of the active ingredient, tamoxifen. Based on the results of clinical studies, it is believed that the optimum dose is 20 mg per day, which may be achieved by administering 10 mg tablets twice a day or a 20 mg tablet once a day.

Raloxifene is the generic name for 6-hydroxy-2(4-hydroxyphenyl)-3-[4-(2-piperdinoethoxy)benzoyl]benzo[b]thiophene. Raloxifene is generally available as the hydrochloride salt, however other pharmacologically acceptable salts may be used. Raloxifene is produced according to the methods described in U.S. Pat. Nos. 4,418,068 and 4,133,814, the disclosure of which is incorporated by reference. Typically raloxifene is administered orally in tablet for with a dosage of 60 mg of raloxifene hydrochloride.

Toremifene is the generic name for 4-chloro-1,2-diphenyl-1-{4-[2-(N,N-dimethylamino)ethoxy]-phenyl}-1-butene. Toremifene is generally available as the citrate salt, however other pharmacologically acceptable salts may be used. Toremifene may be produced by the methods described in U.S. Pat. No. 4,696,949, the disclosure of which is incorporated herein by reference. Typically toremifene is administered orally at an optimum dosage of 60 mg/day.

The compositions of the present invention are typically prepared as a single dosage form that combines a nonsteroidal antiandrogen and a selective estrogen receptor modulator. Example combinations include 50 mg bicalutamide and 60 mg raloxifene, 50 mg bicalutamide and 20 mg tamoxifen, 50 mg bicalutamide and 60 mg of toremifene, 50 mg nilutamide and 20 mg tamoxifen; and 50 mg nilutamide and 60 mg raloxifene. Preferably, the composition comprises from about 40 to about 200 mg of the non-steroidal antiandrogen or a pharmaceutically acceptable salt thereof and from about 10 to about 80 mg. of the selective estrogen receptor modulator or a pharmaceutically acceptable salt thereof.

The dosage administered is dependent upon the age, weight, kind of concurrent treatment, if any, and nature of the cancer. The selected dosage depends upon the desired effect, on the route of administration and on the duration of the treatment. The dose will vary from patient to patient depending upon the nature and severity of disease, the patient's weight, the patient's special diets, concurrent medications that are being used, and other factors which those skilled in the art will recognize. Based upon the foregoing, precise dosages are left to the discretion of the skilled clinician.

The effective composition useful in the methods of the present invention may be employed in such forms as capsules, tablets, liquid solutions, suspensions or elixirs for oral administration or sterile liquid forms such as solutions, suspensions or emulsions. Any inert carrier is preferably used, such as saline or phosphate buffered saline or any such carrier in which the compounds used in the methods of the present invention have suitable solubility properties.

The novel composition of the present invention may be administered in a pharmaceutically acceptable carrier. The pharmaceutically acceptable carrier is any solvent with which the composition of the present invention is compatible and which is non-toxic to the individuals treated at the amounts administered. A pharmacological dose of the novel composition of the present invention useful in the methods of the present invention is that amount of the nonsteroidal antiandrogen compound and selective estrogen receptor modulator that achieves a synergistic effect on prostate cancer tumors.

Solid dosage forms for oral administration include capsules, tablets, pills, powders and granules. In solid dosage forms, the active compound is typically admixed with at least one inert pharmaceutically acceptable carrier such as sucrose, lactose or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents.

When the dosage form is a capsule, it may contain, in addition to the materials noted above, a liquid carrier such as fatty oil. Various other materials may be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring, if desired.

Preparations according to this invention for parenteral administration include sterile aqueous or non-aqueous solutions, suspensions, or emulsions. Sterile compositions for injection may be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions that can be dissolved in sterile water, or some other sterile injectable medium immediately before use. Compositions for rectal or vaginal administration are preferably suppositories that may contain, in addition to the active substance, excipients such as cocoa butter or a suppository wax. Compositions for nasal or sublingual administration are also prepared with standard excipients well known in the art.

The adjuvant therapy of the present invention is begun shortly after completion of the primary for the prostate cancer, such as radical prostatectomy, radiation treatment, etc., and is continued until there is a reoccurrence of the cancer, such as indicated by a rise in the prostate specific antigen (PSA). The typical time for reoccurrence of prostate cancer is between 36 and 60 months after the primary treatment. If the cancer has not reoccurred within this time, the patient is generally considered cancer free. Therefore, the preferred time for continuation of the adjuvant therapy is between about 36 to about 60 months, since after this period of time the benefits of the therapy compared to the risks involved generally indicate a discontinuance of the therapy.

EXAMPLE 1

A number of patients having non-metastasized prostate cancer who had received electron beam radiation treatment are placed on adjuvant therapy of 50 mg bicalutamide and 60 mg of raloxifene per day for 180 days. These patients are monitored for reoccurrence of symptoms of prostate cancer for a multi-year period. The patients of Example 1 have fewer reoccurrences than either a control group who did not receive adjuvant therapy or the group that received only the bicalutamide.

EXAMPLE 2

The patients of Example 1 are also monitored for side effects including the development of breast tenderness and/or gynecomastia. Compared to a similar population that is treated with 50 mg of bicalutamide per day as a control group, the test group of Example 1 has significantly fewer incidence of either breast tenderness or gynecomastia.

INDUSTRIAL APPLICABILITY

The present invention is useful as an adjuvant therapy in the treatment of prostate cancer.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A method of adjuvant therapy for a patient afflicted by a prostate cancer to reduce the reoccurrence of prostate cancer, comprising the steps of:
   (a) administering a primary treatment to the patient;
   (b) administering a combination of a therapeutically effective amount of bicalutamide or a pharmaceutically acceptable salt thereof and raloxifene or a pharmaceutically acceptable salt thereof to begin shortly after the primary treatment has been completed; and
   (c) observing the patient for recurrence of the prostate cancer during the continued adjuvant therapy for a period of up to about 60 months.

2. The method of claim 1, wherein the combination comprises from about 40 to about 200 mg of the bicalutamide or a pharmaceutically acceptable salt thereof.

3. The method of claim 2, wherein the combination comprises about 50 mg of the bicalutamide or a pharmaceutically acceptable salt thereof.

4. The method of claim 1, wherein the combination comprises from about 10 to about 80 mg of the raloxifene or a pharmaceutically acceptable salt thereof.

5. The method of claim 4, wherein the combination comprises about 60 mg of the raloxifene or a pharmaceutically acceptable salt thereof.

6. The method of claim 1, wherein the combination comprises about 50 mg of the bicalutamide or a pharmaceutically acceptable salt thereof and about 60 mg of the raloxifene or a pharmaceutically acceptable salt thereof.

7. The method of claim 1, wherein the combination is administered in a unit dosage form.

8. The method of claim 1, wherein the combination is administered at the same time in different dosage forms.

9. The method of claim 1, wherein the bicalutamide or a pharmaceutically acceptable salt thereof is administered in a dosage of between about 50 to about 150 mg/day.

* * * * *